(12) United States Patent
Pursley

(10) Patent No.: US 9,301,828 B1
(45) Date of Patent: Apr. 5, 2016

(54) MULTI LUMEN IVC FILTER RETRIEVAL DEVICE

(71) Applicant: Matt D. Pursley, Dawsonville, GA (US)

(72) Inventor: Matt D. Pursley, Dawsonville, GA (US)

( * ) Notice: Subject to any disclaimer, the term of this patent is extended or adjusted under 35 U.S.C. 154(b) by 0 days.

(21) Appl. No.: 14/214,344

(22) Filed: Mar. 14, 2014

Related U.S. Application Data

(60) Provisional application No. 61/781,007, filed on Mar. 14, 2013.

(51) Int. Cl.
*A61M 29/00* (2006.01)
*A61F 2/01* (2006.01)
*A61B 17/50* (2006.01)

(52) U.S. Cl.
CPC . *A61F 2/01* (2013.01); *A61B 17/50* (2013.01); *A61F 2002/011* (2013.01)

(58) Field of Classification Search
CPC ..... A61F 2/013; A61F 2002/011; A61F 2/01; A61B 2017/320733; A61B 17/32056; A61B 2017/320716; A61B 17/221; A61B 2017/2217; A61B 17/3205; A61B 17/32053; A61M 25/01; A61M 25/04; A61M 25/1002; A61M 2025/018; A61M 2025/0177; A61M 25/09041
USPC ................. 606/200, 110, 113, 114, 127, 159
See application file for complete search history.

(56) References Cited

U.S. PATENT DOCUMENTS

| | | | |
|---|---|---|---|
| 2003/0065335 A1* | 4/2003 | Guido et al. .................. | 606/144 |
| 2005/0154378 A1* | 7/2005 | Teague et al. .................. | 606/2.5 |
| 2007/0038022 A1* | 2/2007 | Nakao ............................ | 600/104 |
| 2011/0118769 A1* | 5/2011 | Bliss et al. .................... | 606/159 |
| 2014/0180267 A1* | 6/2014 | Vetter et al. ..................... | 606/33 |

* cited by examiner

*Primary Examiner* — Katrina Stransky
(74) *Attorney, Agent, or Firm* — Jeffrey L. Thompson; Thompson & Thompson, P.A.

(57) ABSTRACT

A device for retrieving items endovascularly includes a sheath having a first lumen containing a snare that can be deployed out a distal end of the sheath and retracted back into the sheath for pulling an IVC filter into the sheath. The sheath has a second lumen that opens through a sidewall of the sheath proximal of the distal end. The second lumen contains a removal assist device that can be deployed through the sidewall and used to dislodge and/or cut an item to be retrieved from a vein wall. The removal assist device includes a catheter, a cutting head, and a pull wire. The pull wire has a proximal portion protruding from a proximal end of the catheter and a distal end connected to the cutting head. The pull wire is movable within the catheter to selectively extend and retract the cutting head from the distal end of the catheter.

6 Claims, 4 Drawing Sheets

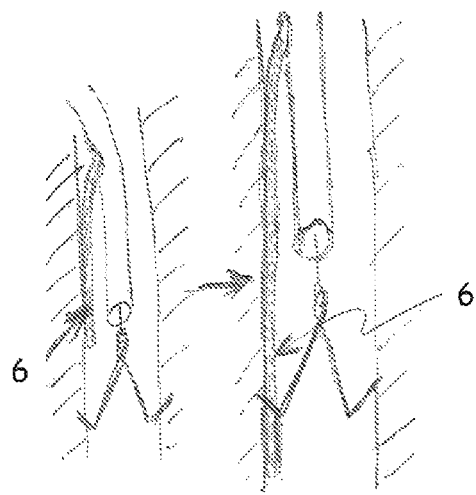
Fig. 5A    Fig. 5B
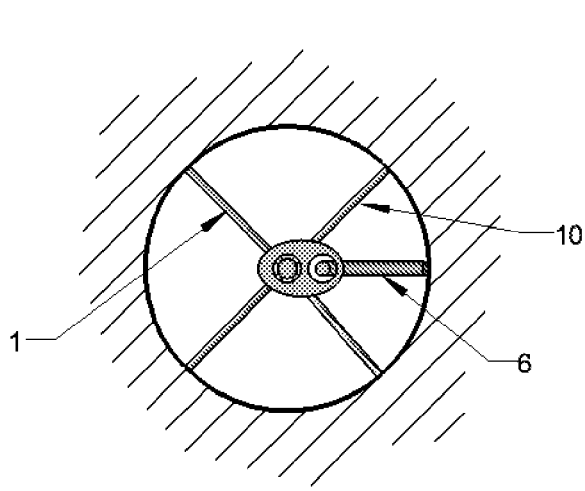
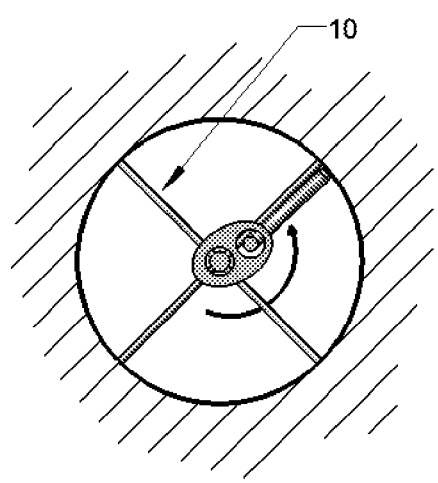
Fig. 6A    Fig. 6B

MULTI LUMEN IVC FILTER RETRIEVAL DEVICE

RELATED APPLICATIONS

This application claims the benefit of U.S. Provisional Patent Application No. 61/781,007 filed on Mar. 14, 2013. The entire content of the priority application is incorporated herein by reference.

BACKGROUND OF THE INVENTION

1. Field of the Invention

The present invention relates generally to catheters, and in particular to catheters that can be used to assist in removal of items endovascularly.

2. Description of the Related Art

Inferior vena cava filters ("IVC filters") are medical devices that can be implanted into the inferior vena cava to prevent pulmonary emboli (PE). IVC filters are sometimes recommended for patients with contraindications to anticoagulation who either have acute PE or acute proximal (above the knee) deep vein thrombosis. IVC filters are normally placed by compressing them into a thin catheter, and inserting them via a blood vessel, such as the femoral vein, the internal jugular vein, or the arm veins. Once the distal end of the catheter reaches the IVC, the IVC filter is pushed through the catheter and deployed into the desired location.

IVC filters are typically attached to the vena cava by hooks on their ends. Some IVC filters are compression springs, which compress outward onto the sidewall of the vena cava; however, they still have small hooks that retain their location. These hooks aid in the anchoring and healing process, but they make it difficult to retrieve the IVC filter from the vena cava.

FIG. 1 shows an IVC filter 1 deployed in the inferior vena cava. IVC filters 1 are generally anchored by anchors 4 to prevent them from migrating. IVC filters 1 are removed by using a snare 2 and a retrieval sheath 3. Coupling the snare with the IVC filter 1 is difficult. The IVC filter 1 may not be vertically aligned making it difficult to snare. Body movement due to respiration and blood flow also make snaring the IVC filter 1 difficult.

As can be seen in FIG. 1, the snare 2 is attached to the top of the filter 1. As shown in FIG. 2, the sheath 3 is pushed down over the filter 1, capturing the filter 1 and its contents and removing the filter anchors 4 from the vein wall. This allows the filter 1 to be removed. However, on occasion the filter anchors 4 or a portion of the filter 1 become embedded to the vein wall, and this removal procedure cannot be performed.

There is a need for an improved tool to assist with the removal of IVC filters.

SUMMARY OF THE INVENTION

An object of the present invention is to provide a device and method for assisting with the removal of IVC filters.

To accomplish these and other objects of the present invention, a device for retrieving items endovascularly includes a sheath having a first lumen containing a snare that can be deployed out a distal end of the sheath and retracted back into the sheath for pulling an IVC filter into the sheath. The sheath has a second lumen that opens through a sidewall of the sheath proximal of the distal end. The second lumen contains an additional device, such as a balloon, imaging device, diagnostic catheter for infusing contrast media, or a removal assist device. The removal assist device can be deployed through the sidewall and used to dislodge and/or cut an item to be retrieved from a vein wall. The removal assist device includes a catheter, a cutting head, and a pull wire. The pull wire has a proximal portion protruding from a proximal end of the catheter and a distal end connected to the cutting head. The pull wire is movable within the catheter to selectively extend and retract the cutting head from the distal end of the catheter.

According to one aspect of the present invention, a device for retrieving items endovascularly is provided, comprising: a sheath having a first lumen containing a snare that can be deployed out a distal end of the sheath and retracted back into the sheath; the sheath having a second lumen that opens through a sidewall of the sheath proximal of the distal end.

Numerous other objects of the present invention will be apparent to those skilled in this art from the following description wherein there is shown and described an embodiment of the present invention, simply by way of illustration of one of the modes best suited to carry out the invention. As will be realized, the invention is capable of other different embodiments, and its several details are capable of modification in various obvious aspects without departing from the invention. Accordingly, the drawings and description should be regarded as illustrative in nature and not restrictive.

BRIEF DESCRIPTION OF THE DRAWINGS

The present invention will become more clearly appreciated as the disclosure of the invention is made with reference to the accompanying drawings. In the drawings:

FIGS. 5A and 5B are a sequence of side elevation views showing a removal assist catheter being deployed out of the IVC filter retrieval device of the present invention.

FIGS. 6A and 6B are a sequence of top views showing the filter retrieval device of the present invention being rotated to cause the removal assist catheter to engage an IVC filter strut.

DETAILED DESCRIPTION OF THE INVENTION

A multi lumen IVC filter retrieval device according to the present invention will be described in detail with reference to FIGS. 3 to 6B of the accompanying drawings.

Figure 1:
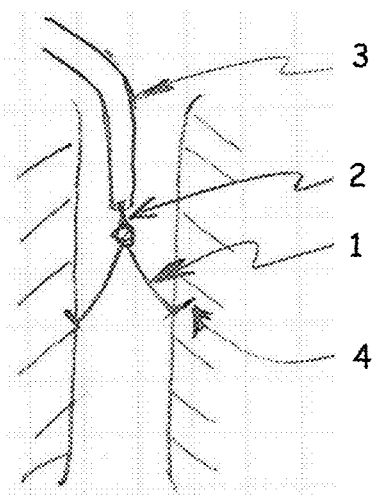
FIG. 1 is illustrates a conventional retrieval sheath for removing an IVC filter deployed in the inferior vena cava.
Figure 2:
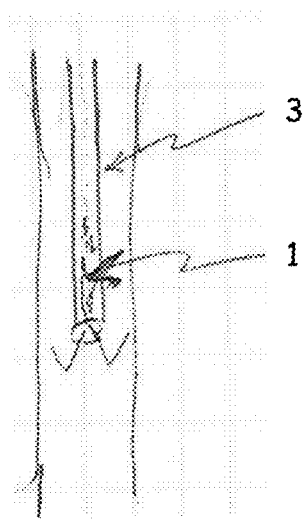
FIG. 2 illustrates the process of using the conventional retrieval sheath shown in FIG. 1.
Figure 3:
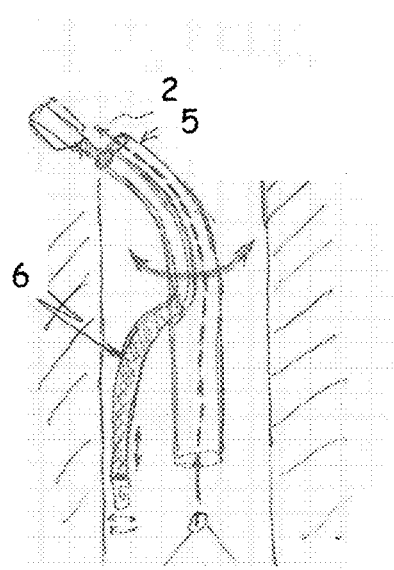
FIG. 3 is an elevation view of a multi lumen IVC filter retrieval device of the present invention as it is being deployed to a location above an IVC filter to be removed.
Figure 4:
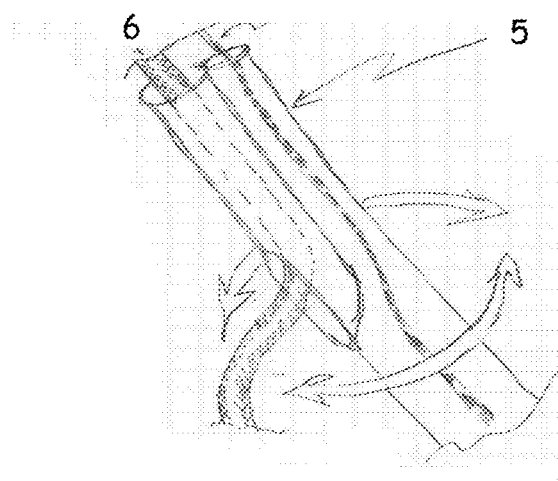
FIG. 4 is a perspective view of the multi lumen IVC filter retrieval device of the present invention.

The multi lumen IVC filter retrieval device is shown in FIGS. 3 and 4. As can be seen, the device uses the same snare and sheath concept as in the conventional flter retrieval device illustrated in FIGS. 1 and 2, except that it also adds a lumen in the proximal portion of the sheath through which additional devices can be passed, such as balloons, imaging devices, diagnostic catheters for infusing contrast media, or a removal assist device 6, if necessary.

Figure 7:
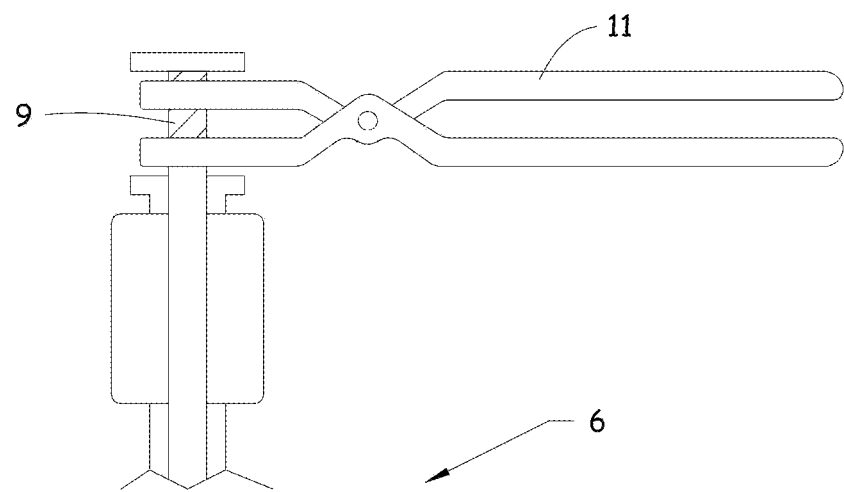
FIG. 7 is an elevation view of the removal assist device with the cutting head being used to grip and/or cut an IVC filter strut, and a cutter actuator at a proximal end for actuating the device.
Figure 7:
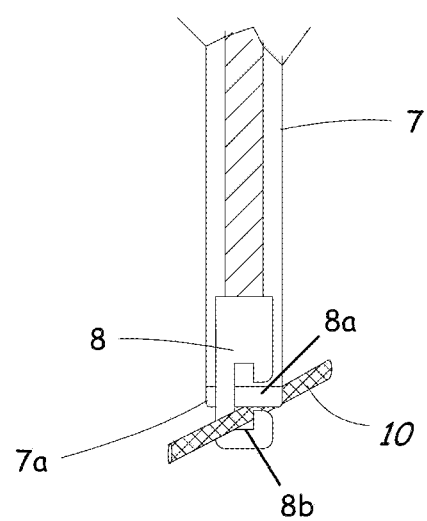

The removal assist device 6 is described and illustrated in Applicant's copending U.S. Utility patent application Ser. No. 14/214,273 filed on Mar. 14, 2014, the contents of which are hereby incorporated by reference. As illustrated in FIGS. 3 and 7, the removal assist device 6 includes a catheter 7, a cutting head 8, and a pull wire 9 to actuate and/or retract the cutting head 8. The cutting head 8 can also be referred to as a holding/cutting head because it serves a dual function of holding and cutting the items to be removed. The cutting head 8 has a generally C-shaped structure with an open lateral side 8a for receiving a portion of an item 10 to be held or cut. The C-shaped structure has a distal portion and a proximal portion with the open lateral side 8a located between the distal portion and the proximal portion. The distal portion of the C-shaped structure has a sharpened inner edge 8b facing in a proximal direction, which functions to cut through an item 10 when the item is held against the distal end 7a of the catheter 7 and a pulling force is applied to the pull wire 9. The device is intended to give a physician the ability to enter a cavity, such as a vein, and make contact with and hold or cut an item, such as an IVC filter or an IVC filter strut.

The cutting head 8 can be retracted into the catheter 7 of the removal assist device 6 for deployment or removal. This prevents the cutting head 8 from snagging on things as it is deployed, removed or repositioned during a procedure. The device 6, with the cutting head 8 in its retracted position within the catheter 7, can easily be pushed past an item, such as an IVC filter. The cutting head 8 can then be extended from the distal end 7a of the catheter 7. The physician can pull the cutting head 8 back while positioning it against the item to be removed until the cutting head 8 engages the item or portion of the item, such as an IVC filter strut 10. The cutting head 8 can then be partially retracted to grasp the item 10 as shown. Once the item 10 has been grasped, the physician can then use the catheter 7 to push/pull/rotate the item 10 and attempt to dislodge it.

If the physician is unable to dislodge the item 10, a cutter actuator 11 (FIG. 7) can be engaged to the proximal end of the catheter 7 and pull wire 9 of the removal assist device 6. The actuator 11 can be used to increase the amount of force applied to the pull wire 9 to cause the cutting head 8 to cut the item 10, thereby freeing it. The cutting head 8 can then be retracted into the catheter 8 and repositioned to other items or portions of the same item that need assistance in freeing for removal.

The additional lumen of the filter retrieval device of the present invention is oriented so any additional device or catheter, such as the removal assist catheter 6, which is inserted to assist in removal, is directed towards the vein wall, thereby preventing entrapment of the additional device in the filter itself.

A key feature of this filter retrieval device 5 is the fact that it can be rotated about its axis allowing the removal assist catheter 6 to be swept along the vein wall to engage the legs, struts or embedded portion of the IVC filter.

The filter retrieval device 5 can be used by inserting the device 5 into the vasculature as is done with current sheaths (see FIG. 5A). A snare can be used to engage the IVC filter as is conventionally done. If the physician experiences difficulty in snaring the IVC filter, a balloon can be inserted in the additional lumen and inflated to stabilize the filter, and further attempts can be made to snare the filter. A diagnostic catheter can be inserted to infuse contrast media for external imaging. Additionally, an imaging catheter, such as an intravascular ultrasound catheter, can be used to assist in snaring the IVC filter. Once snared, if the IVC filter or portion of the IVC filter will not disengage from the vein wall, the physician can then use the additional lumen of the device 5 to insert a removal assist catheter, such as a cutter or a laser, to aid in removal of the filter.

FIGS. 5A and 5B show the multi-lumen filter retrieval device 5 with the snare attached to the IVC filter. Also shown in FIGS. 5A and 5B is a removal assist catheter 6 extended though the multi-lumen sheath.

The physician can advance the removal assist catheter 6 past the filter (FIG. 5B) and then rotate the device 5 until the removal assist catheter 6 makes contact with the filter strut 10 (see FIGS. 6A and 6B). The physician can then pull the removal assist catheter 6 back until it engages the filter. The physician can then use the removal assist catheter 6 to try and dislodge the filter from the vein wall or sever the filter at the vein wall.

The removal assist catheter 6 can then be rotated/retracted/extended until it makes contact with another embedded portion of the filter where the next section could be dislodged or severed. This process can be repeated until the filter is completely dislodged from the vein wall, which can be verified by rotating the multi-lumen device 5 360 degrees, ensuring there are no remaining portions of the filter lodged in the vein wall. This ability to rotate the device will also aid in positioning a balloon or imaging device during the procedure.

While the invention has been specifically described in connection with a specific embodiment thereof, it is to be understood that this is by way of illustration and not of limitation, and the scope of the appended claims should be construed as broadly as the prior art will permit.

What is claimed is:

1. A device for retrieving items endovascularly, comprising:
    a sheath having a first lumen containing a snare that can be deployed out a distal end of the sheath and retracted back into the sheath;
    said sheath having a second lumen that opens through a sidewall of the sheath proximal of the distal end;
    wherein said second lumen contains a removal assist device that can be deployed through the sidewall of the sheath and used to dislodge and/or cut an item to be retrieved from a vein wall;
    wherein said removal assist device is a removal assist catheter having a pull wire and a cutting head attached to the pull wire that can be extended out a distal end of the catheter and used to hold and/or cut an item to be retrieved; and
    wherein said cutting head comprises a generally C-shaped structure having an open lateral side for receiving a portion of an item to be held or cut.

2. The device according to claim 1, wherein said C-shaped structure has a distal portion and a proximal portion with said open lateral side located between said distal portion and said proximal portion, and said distal portion of said C-shaped structure has a sharpened inner edge facing in a proximal direction which is arranged to cut through an item when the item is held within the C-shaped structure against the distal end of the catheter and a pulling force is applied to the pull wire.

3. The device according to claim 1, wherein said sheath is rotatable about its longitudinal axis to allow the removal assist catheter to be swept along a vein wall to engage an item to be retrieved.

4. A multi lumen IVC filter retrieval device, comprising:
    a sheath having a first lumen containing a snare that can be deployed out a distal end of the sheath and retracted back into the sheath;
    said sheath having a second lumen that opens through a sidewall of the sheath proximal of the distal end, and said second lumen contains a removal assist device that can be deployed through the sidewall of the sheath and used to dislodge and/or cut an IVC filter to be retrieved from a vein wall;

wherein said removal assist device is a removal assist catheter having a pull wire and a cutting head attached to the pull wire that can be extended out a distal end of the catheter and used to hold and/or cut the IVC filter to be retrieved; and wherein said cutting head comprises a generally C-shaped structure having an open lateral side for receiving a portion of the IVC filter to be retrieved.

5. The device according to claim 4, wherein said C-shaped structure has a distal portion and a proximal portion with said open lateral side positioned between said distal portion and said proximal portion, and said distal portion of said C-shaped structure has a sharpened inner edge facing in a proximal direction which is arranged to cut through a portion of the IVC filter when the portion of the IVC filter is held within the C-shaped structure against the distal end of the catheter and a pulling force is applied to the pull wire.

6. The device according to claim 4, wherein said sheath is rotatable about its longitudinal axis to allow the removal assist catheter to be swept along a vein wall to engage the IVC filter to be retrieved.

\* \* \* \* \*